(12) United States Patent
McMillen et al.

(10) Patent No.: US 6,833,444 B2
(45) Date of Patent: Dec. 21, 2004

(54) KETOLIDE ANTIBIOTICS

(75) Inventors: William T. McMillen, Fishers, IN (US); Takushi Kaneko, Guilford, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/116,969

(22) Filed: Apr. 5, 2002

(65) Prior Publication Data

US 2002/0156027 A1 Oct. 24, 2002

Related U.S. Application Data

(63) Continuation of application No. 09/491,804, filed on Jan. 26, 2000, now abandoned.
(60) Provisional application No. 60/117,342, filed on Jan. 27, 1999.

(51) Int. Cl.[7] .............................................. C07H 17/08
(52) U.S. Cl. ........................................................ 536/7.4
(58) Field of Search ............................. 536/7.4; 519/29

(56) References Cited

U.S. PATENT DOCUMENTS

| | | | | |
|---|---|---|---|---|
| 4,474,768 A | 10/1984 | Bright | | 424/180 |
| 4,517,359 A | 5/1985 | Kobrehel et al. | | 536/7.4 |
| 5,141,926 A | 8/1992 | Weber et al. | | 514/29 |
| 5,527,780 A | 6/1996 | Agouridas et al. | | 514/29 |
| 5,543,400 A | 8/1996 | Agouridas et al. | | 514/29 |
| 5,561,118 A | 10/1996 | Agouridas et al. | | 514/29 |
| 5,614,614 A | 3/1997 | Agouridas et al. | | 536/7.5 |
| 5,635,485 A | * 6/1997 | Agouridas et al. | | 514/29 |
| 5,747,466 A | 5/1998 | Elliott et al. | | 514/29 |
| 5,747,467 A | * 5/1998 | Agouridas et al. | | 514/29 |
| 5,786,339 A | * 7/1998 | Agouridas et al. | | 514/30 |
| 5,866,549 A | 2/1999 | Or et al. | | 514/29 |
| 6,022,965 A | 2/2000 | Benedetti et al. | | 536/125 |
| 6,096,714 A | 8/2000 | Agouridas et al. | | 514/29 |
| 6,100,240 A | 8/2000 | Cheng et al. | | 514/29 |
| 6,121,432 A | 9/2000 | Bonnet et al. | | 536/7.2 |
| 6,159,945 A | 12/2000 | Wu | | 514/29 |
| 6,162,793 A | 12/2000 | Agouridas et al. | | 514/29 |
| 6,165,986 A | 12/2000 | Asaka et al. | | 514/29 |
| 6,313,101 B1 | 11/2001 | Denis et al. | | 514/29 |
| 6,355,620 B1 | 3/2002 | Ma et al. | | 514/29 |
| 6,399,582 B1 | 6/2002 | Hlasta et al. | | 514/29 |
| 6,420,343 B1 | 7/2002 | Su et al. | | 514/29 |
| 6,440,941 B1 | 8/2002 | Denis | | 514/29 |
| 6,593,302 B2 | 7/2003 | Chu et al. | | 514/29 |
| 6,664,238 B1 | 12/2003 | Su et al. | | 514/29 |
| 2002/0013281 A1 | 1/2002 | Agouridas et al. | | 514/29 |
| 2002/0025937 A1 | 2/2002 | Wu | | 514/29 |
| 2002/0040007 A1 | 4/2002 | Kaneko | | 514/28 |
| 2002/0052328 A1 | 5/2002 | Kaneko et al. | | 514/29 |
| 2002/0061856 A1 | 5/2002 | Wu | | 514/29 |
| 2003/0013665 A1 | 1/2003 | Kaneko | | 514/29 |
| 2003/0050254 A1 | 3/2003 | Denis | | 3/29 |
| 2003/0100518 A1 | 5/2003 | Wu et al. | | 514/29 |

FOREIGN PATENT DOCUMENTS

| | | | | |
|---|---|---|---|---|
| EP | 1114826 | 7/2001 | | C07H/17/08 |
| EP | 1122261 | 8/2001 | | C07H/17/02 |
| WO | WO 9801546 | 1/1998 | | C12N/15/00 |
| WO | WO 9801571 | 1/1998 | | C12N/15/62 |
| WO | WO 9825942 | 6/1998 | | C07H/17/08 |
| WO | WO 9838199 | 9/1998 | | C07H/17/08 |
| WO | WO 9911651 | 3/1999 | | C07H/17/00 |
| WO | WO 9921869 | 5/1999 | | C07H/17/08 |
| WO | WO 9925385 | 5/1999 | | A61K/31/70 |
| WO | WO 9935157 | 7/1999 | | C07H/17/08 |
| WO | WO 0027857 | 5/2000 | | C07H/17/08 |
| WO | WO 0044761 | 8/2000 | | C07H/17/00 |
| WO | WO 0063224 | 10/2000 | | C07H/17/08 |
| WO | WO 0063225 | 10/2000 | | C07H/17/08 |

* cited by examiner

*Primary Examiner*—Elli Peselev
(74) *Attorney, Agent, or Firm*—Peter C. Richardson; Gregg C. Benson; Frank W. Forman

(57) ABSTRACT

This invention relates to compounds of the formula 1:

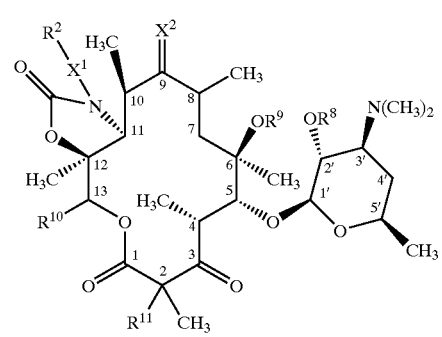

and to pharmaceutically acceptable salts and solvates thereof wherein $X^1$, $X^2$, $R^2$, $R^8$, $R^9$, $R^{10}$ and $R^{11}$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1 and to methods of treating bacterial and protozoal infections by administering the compounds of formula 1.

5 Claims, No Drawings

KETOLIDE ANTIBIOTICS

This is a continuation application based upon and claiming priority from U.S. patent application Ser. No. 09/491,804, filed Jan. 26, 2000, now abandoned which is based upon U.S. Provisional Application No. 60/117,342, filed Jan. 27, 1999.

BACKGROUND OF THE INVENTION

This invention relates to novel macrolide compounds that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Macrolide antibiotics are known to be useful in the treatment of a broad sprectrum of bacterial and protozoal infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Other macrolide antibiotics are disclosed and claimed in PCT international published application WO 98/56800 (published Dec. 17, 1998), which designates the United States; U.S. Pat. No. 5,527,780, issued Jun. 18, 1996; U.S. provisional application No. 60/101,263 (filed Sep. 22, 1998)(attorney docket No. PC 10406); U.S. provisional patent application No. 60/111,728 (filed Dec. 10, 1998) (attorney docket No. PC 10494); PCT published application WO 98/01546 (published Jan. 15, 1998); PCT published application WO 98/01571 (published Jan. 15, 1998); EP published application No. 949268 (published Oct. 13, 1999); and U.S. Pat. No. 5,747,467 (issued May 5, 1998). Each of the foregoing United States patents and patent applications and published EP and PCT international patent applications are incorporated herein by reference in their entirety. Like azithromycin and other macrolide antibiotics, the novel macrolide compounds of the present invention possess activity against various bacterial and protozoal infections as described below.

SUMMARY OF THE INVENTION

The present invention relates to compounds of the formula:

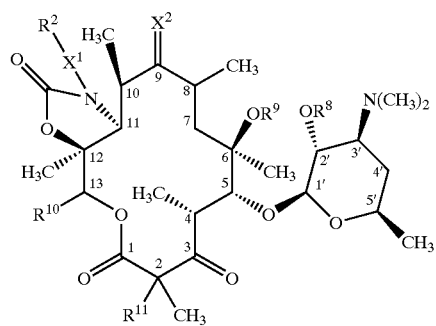

and to pharmaceutically acceptable salts and solvates thereof, wherein:

$X^1$ is O, —$CR^4R^5$— or —$NR^4$—;

$X^2$ is =O or =$NOR^1$;

$R^1$ is H or $C_1$–$C_{10}$ alkyl, wherein 1 to 3 carbons of said alkyl are optionally replaced by a heteroatom selected from O, S and —N($R^4$)—, and said alkyl is optionally substituted by 1 to 3 substituents independently selected from the group consisting of —C(O)O($C_1$–$C_{10}$ alkyl), $C_1$–$C_{10}$ alkoxy, $C_1$–$C_{10}$ alkanoyl, halo, nitro, cyano, 4–10 membered heterocyclyl, $C_1$–$C_{10}$ alkyl, —$NR^4R5^5$, $C_6$–$C_{10}$ aryl, —S(O)$_n$($C_1$–$C_{10}$ alkyl) wherein n is an integer ranging from 0 to 2, and —$SO_2NR^4R^5$;

$R^2$ is —$(CR^4R^5)_n$(4–10 membered heterocyclic) or —$(CR^4R^5)_n$($C_6$–$C_{10}$ aryl), wherein n is an integer from 0 to 6, from 1 to 3 $R^4$ or $R^5$ groups of the —$(CR^4R^5)_n$—moiety of the foregoing $R^2$ groups are optionally replaced with a halo substituent, and the heterocyclic and aryl moieties of the foregoing $R^2$ groups are optionally substituted with 1 to 4 $R^3$ groups;

each $R^3$ is independently selected from halo, cyano, nitro, trifluoromethoxy, trifluoromethyl, azido, hydroxy, $C_1$–$C_6$ alkoxy, $C_1$–$C_{10}$ alkyl, $C_2$–$C_6$ alkenyl, $C_2$–$C_6$ alkynyl, —C(O)$R^6$, —C(O)O$R^6_1$, —OC(O)$R^6$, —$NR^6$C(O)$R^7$, —$NR^6$C(O)$NR^1R^7$, —$NR^6$C(O)O$R^7$, —C(O)$NR^6R^7$, —$NR^6R^7$, —$NR^6$O$R^7$, —$SO_2NR^6R^7$, —S(O)$_j$($C_1$–$C_6$ alkyl) wherein j is an integer from 0 to 2, —$(CR^1R^2)_t$($C_6$–$C_{10}$ aryl), —$(CR^4R^5)_t$(4–10 membered heterocyclic), —$(CR^4R^5)_q$C(O) $(CR^4R^5)_t$ ($C_6$–$C_{10}$ aryl), —$(CR^4R^5)_q$C(O)($CR^4R^5)_t$(4–10 membered heterocyclic), —$(CR^4R^5)_t$O($CR^4R^5)_q$($C_6$–$C_{10}$ aryl), —$(CR^4R^5)_t$O($CR^4R^5)_q$(4–10 membered heterocyclic), —$(CR^4R^5)_q$SO$_2$($CR^4R^5)_t$($C_6$–$C_{10}$ aryl), and —$(CR^4R^5)_q$SO$_2$($CR^4R^5)_t$(4–10 membered heterocyclic), wherein q and t are each independently an integer from 0 to 5, 1 or 2 ring carbon atoms of the heterocyclic moieties of the foregoing $R^{10}$ groups are optionally substituted by an oxo (=O) moiety, and the alkyl, alkenyl, alkynyl, aryl and heterocyclic moieties of the foregoing $R^{10}$ groups are optionally substituted by 1 to 3 substituents independently selected from halo, cyano, nitro, trifluoromethyl, trifluoromethoxy, azido, —O$R^6$, —C(O)$R^6$, —C(O)O$R^6$, —OC(O)$R^6$, —$NR^6$C(O)$R^7$, —C(O)$NR^6R^7$, —$NR^6R^7$, —$NR^6$O$R^7$, $C_1$–$C_6$ alkyl, $C_2$–$C_6$ alkenyl, $C_2$–$C_6$ alkynyl, —$(CR^4R^5)_t$ ($C_6$–$C_{10}$ aryl), and —$(CR^4R^5)_t$(4–10 membered heterocyclic), wherein t is an integer from 0 to 5;

each $R^4$ and $R^5$ is independently selected from H and $C_1$–$C_6$ alkyl;

each $R^6$ and $R^7$ is independently selected from H, $C_1$–$C_6$ alkyl, —$(CR^4R^5)_t$($C_6$–$C_{10}$ aryl), and —$(CR^4R^5)_t$(4–10 membered heterocyclic), wherein t is an integer from 0 to 5, 1 or 2 ring carbon atoms of the heterocyclic group are optionally substituted by an oxo (=O) moiety, and the alkyl, aryl and heterocyclic moieties of the foregoing $R^6$ and $R^7$ groups are optionally substituted by 1 to 3 substituents independently selected from halo, cyano, nitro, —$NR^4R^5$, trifluoromethyl, trifluoromethoxy, $C_1$–$C_6$ alkyl, $C_2$–$C_6$ alkenyl, $C_2$–$C_6$ alkynyl, hydroxy, and $C_1$–$C_6$ alkoxy;

$R^8$ is H, —C(O)($C_1$–$C_6$ alkyl), benzyl, benzyloxycarbonyl or ($C_1$–$C_6$ alkyl)$_3$silyl;

$R^9$ is $C_1$–$C_6$ alkyl;

$R^{10}$ is H or $C_1$–$C_{10}$ alkyl; and $R^{11}$ is selected from chloro, bromo, iodo, fluoro, and cyano;

with the proviso that where $X^2$ is =O then the $R^{11}$ is cyano or from 1 to 3 $R^4$ or $R^5$ groups of the —$(CR^4R^5)_n$—moiety of the $R^2$ groups recited above are either $C_1$–$C_6$ alkyl or replaced with a halo substituent.

Specific embodiments of the present invention include compounds of formula 2 (which is a specific embodiment within the genus of formula 1)

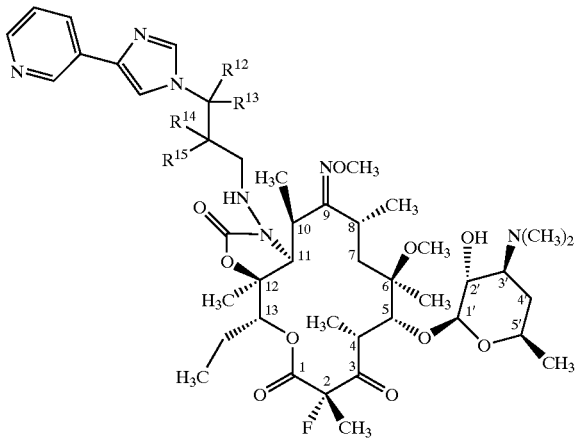

2 wherein $R^{12}$, $R^{13}$, $R^{14}$ and $R^{15}$ are each independently selected from H, halo, methyl and ethyl. More specific embodiments include the compounds of formula 2 wherein $R^{14}$ and $R^{15}$ are both H and $R^{12}$ and $R^{13}$ are each independently selected from H and methyl. In a preferred embodiment of the compounds of formula 2, $R^{12}$, $R^{13}$, $R^{14}$ and $R^{15}$ are each H.

Other specific embodiments of the present invention include compounds of formula 3 (which is a specific embodiment within the genus of formula 1):

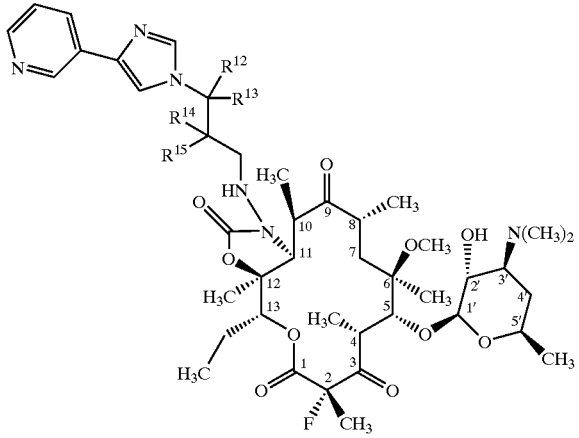

3 wherein $R^{12}_1$, $R^{13}$, $R^{14}$ and $R^{15}$ are each independently selected from H, halo, methyl and ethyl with the proviso that at least one of $R^{12}$, $R^{13}$, $R^{14}$ and $R^{15}$ is not H. More specific embodiments include the compounds of formula 3 wherein $R^{14}$ and $R^{15}$ are both H, $R^{12}$ is methyl, and $R^{13}$ is selected from H and methyl.

The invention also relates to a pharmaceutical composition for the treatment of a bacterial infection or a protozoa infection, or a disorder related to a bacterial or protozoal infection, in a mammal, fish, or bird, which comprises a therapeutically effective amount of a compound of formula 1, or a pharmaceutically acceptable salt or solvate thereof, and a pharmaceutically acceptable carrier.

The invention also relates to a method of treating a bacterial infection or a protozoa infection, or a disorder related to a bacterial or protozoal infection, in a mammal, fish, or bird which comprises administering to said mammal, fish or bird a therapeutically effective amount of a compound of formula 1 or a pharmaceutically acceptable salt or solvate thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E faecium, E. casseltlavus, S. epidertnidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E faecium, E. durans,* including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-negative *staphylococci* (i.e., *S. epidermidis, S. hemolyticus,* etc.), *Streptococcus pyogenes, Streptococcus agalactiae,* Streptococcal groups C–F (minute-colony *streptococci*), viridans streptococci, *Corynebacterium minutissimum, Clostridium* spp., or *Bartonella henselae*; uncomplicated acute urinary tract infections related to infection by *Staphylococcus aureus*, coagulase-negative *staphylococcal* species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and *C streptococci*; ulcers related to infection by *Helicobacter* pylori; systemic febrile syndromes related to infection by *Borrelia recurrentis*; Lyme disease related to infection by *Borrelia burgdorfeni;* conjunctivitis, keratitis, and dacrocystitis related to infection by *Chlamydia trachomatis, Neisseria gononhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or *Bordetella* spp.; cow enteric disease related to infection by *E. coli* or protozoa (i.e., *coccidia, cryptosporidia*, etc.); dairy cow mastitis related to infection by *S. aureus, Strep. uberis, Streptococcus agalactiae, Streptococcus dysgalactiae, Klebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodysinteriae*; cow footrot related to infection by *Fusobacterium* spp.; cow metritis related to infection by *E. coli*, cow hairy warts related to infection by *Fusobacterlum necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S. intermedius, coagulase* neg. *Staphylococcus* or *P. multocida*; and dental or mouth infections in dogs and cats related to infection by *Alcaligenes* spp., *Bacteroides* spp., *Clostddium* spp., *Enterobacter* spp., *Eubactedum, Peptostreptococcus, Porphyromonas*, or *Prevotella*. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having cyclic, straight and/or branched moieties. It is to be understood that to include cyclic moieties, the alkyl group must include at least 3 carbon atoms.

The term "alkenyl", as used herein, unless otherwise indicated, includes alkyl groups as defined above having at least one carbon-carbon double bond at some point in the alkyl chain.

The term "alkynyl", as used herein, unless otherwise indicated, includes alkyl groups as defined above having at least one carbon-carbon triple bond at some point in the alkyl chain.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic-heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo [4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula 1, and pharmaceutically acceptable salts thereof, wherein the radiolabel is selected from $^3$H, $^{11}$C and $^{14}$C. Such radiolabelled compounds are useful as research or diagnostic tools.

Certain compounds of formula 1 may have asymmetric centers and therefore exist in different enantiomeric forms.

This invention relates to the use of all optical isomers and stereoisomers of the compounds of formula 1 and mixtures thereof. In particular, the invention includes both the E and Z isomers of the —OR$^1$ group (where X$^2$ is =NOR$^1$) connected to the nitrogen of the oxime moiety at C-9 of the macrolide ring of formula 1.

The present invention also includes isotopically-labelled compounds, and the pharmaceutically acceptable salts thereof, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages-resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, omithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

DETAILED DESCRIPTION OF THE INVENTION

The preparation of the compounds of the present invention is illustrated in the following Schemes.

Scheme 1

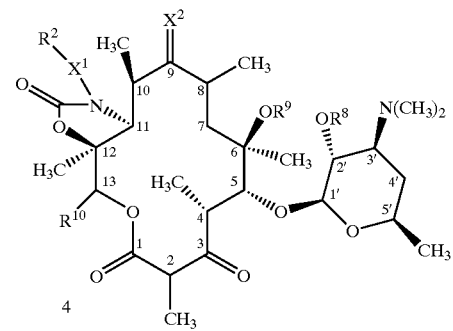

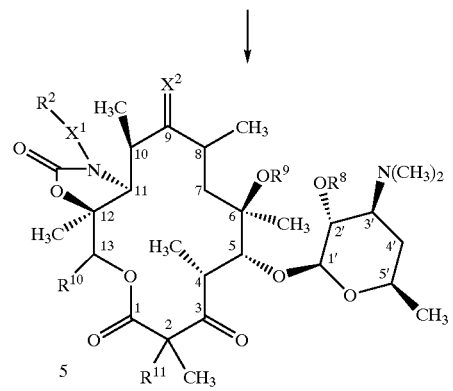

9
-continued
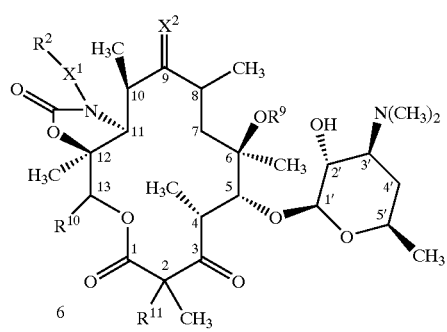
6
Scheme 2
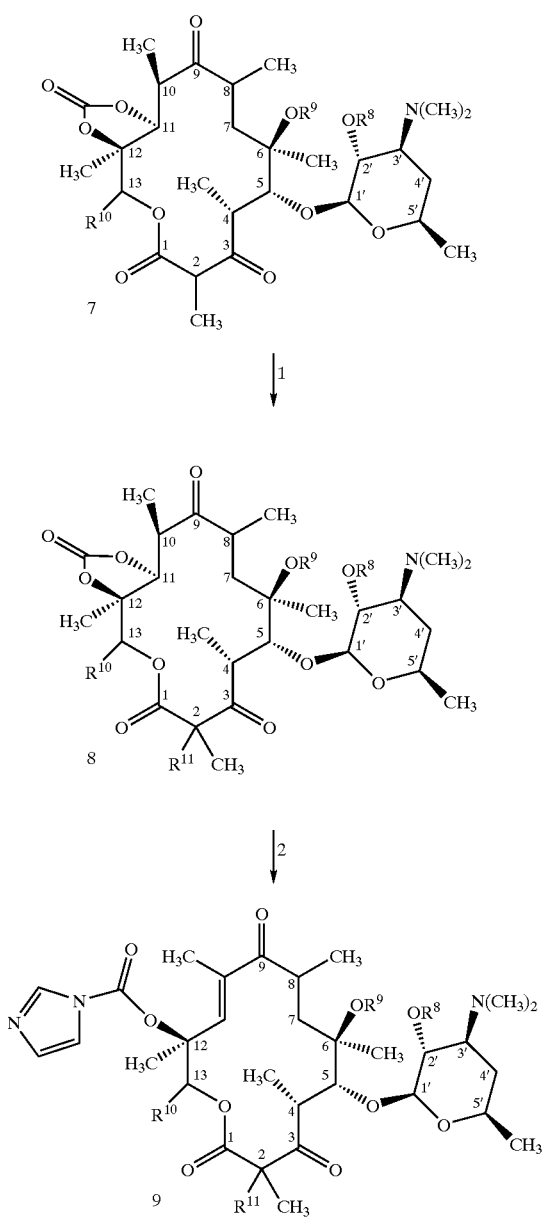
10
-continued
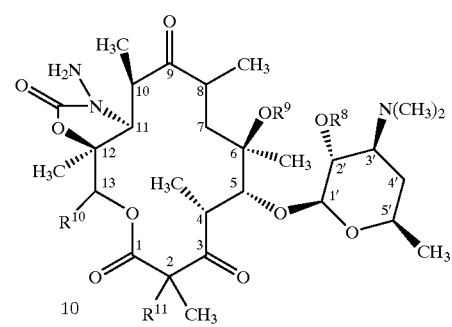
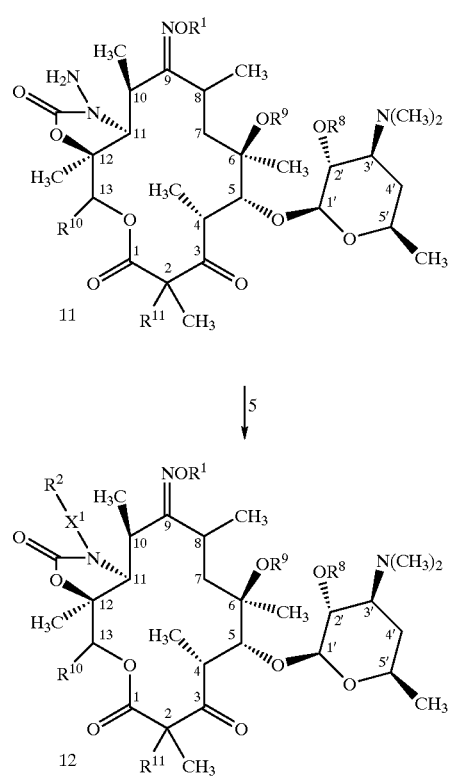
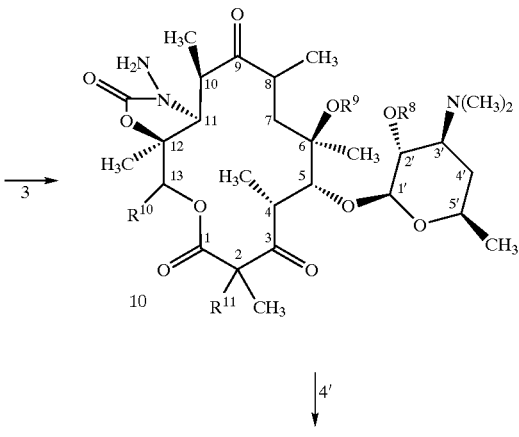

-continued

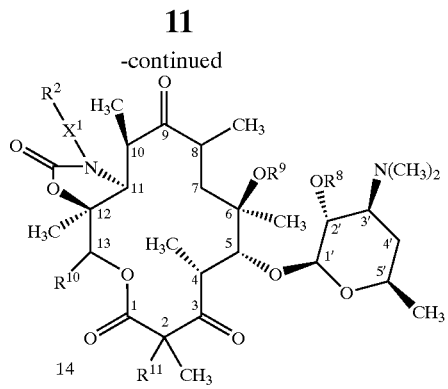
14

Scheme 3

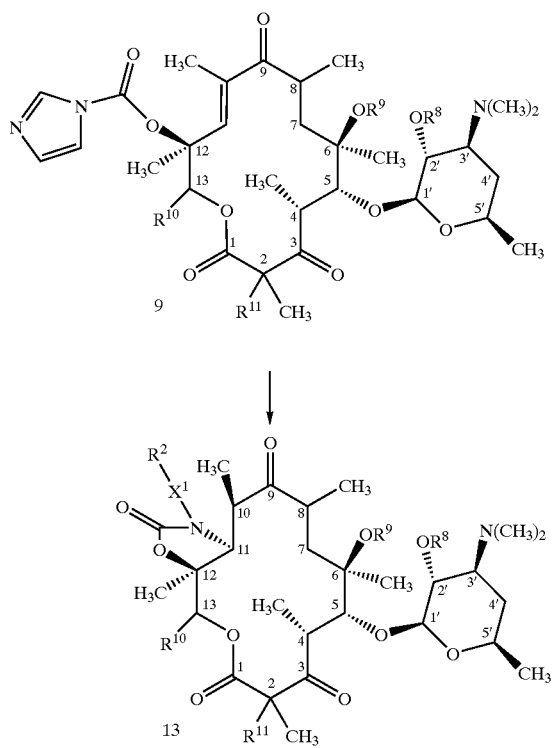

The preparation of the compounds of the present invention is illustrated in the above schemes. Starting materials and/or final compounds of formula 1 wherein $R^{10}$ is a moiety other than ethyl within the definition of $R^{10}$ provided above may be prepared as described in PCT published applications WO 98/01571 (Biotica Tech. Ltd. and Pfizer Inc.) and WO 98/01546 (assigned to Biotica Tech. Ltd.). Other specific methods that relate to the synthesis of the compounds of the present invention are referred to in PCT international patent application publication number WO 98/38199 (published Sep. 3, 1998), PCT international patent application publication number WO 98/56800 (published Dec. 17, 1998), U.S. provisional patent application No. 60/101,263 (filed Sep. 22, 1998), U.S. provisional patent application No. 60/111,728 (filed Dec. 10, 1998), European patent application number EP 487,411, and European patent application number EP 799,833. In the above Schemes, all substituents are as defined for formula 1 referred to above except otherwise indicated.

The starting materials may or may not require proper functional group protection before various modifications can take place, and deprotection after desired modifications are complete. The most commonly used protecting groups for amino moieties in the macrolide compounds of this invention are benzyloxycarbonyl (Cbz) and t-butyloxycarbonyl (Boc) groups. Hydroxyl groups are generally protected as acetates, Cbz carbonates or with a trialklylsilyl group. The C-2' hydroxyl group is a potentially reactive hydroxyl group among the numerous hydroxyl groups present in macrolide compounds of the type claimed herein. The C-2' hydroxyl group is selectively protected by treating the compound with one equivalent of acetic anhydride in dichloromethane in the absence of external base. This process selectively converts the C-2' hydroxyl group into the corresponding acetate. The hydroxyl protecting group can be removed by treating the compound with methanol at a temperature ranging from about 0° C. to 40° C. to about 65° C. for 10 to 48 hours. Other methods of selective protection and deprotection are familiar to those skilled in the art.

With reference to Scheme 1, the compound of formula 5, wherein $R^{11}$ is a halo group and all other substituents are as defined above, may be prepared by treating the compound of formula 4 with a base, such as sodium hydride, potassium hydride, potassium hexamethyidisilazide (KHMDS), pyridine, sodium carbonate, or lithium diisopropylamide, preferably KHMDS, and a halogenating agent, such as N-fluorobenzensulfoimide, SELECTFLUOR® (marketed by Air Products and Chemicals, Inc., Allentown, Pa., United States of America) for fluorination, pyridinium tribromide or cyanogen bromide for bromination, or hexachloroethane for chlorination, in a solvent, such as in N,N-dimethylformamide (DMF), tetrahydrofuran (THF), $CH_2Cl_2$, or N-methylpyrrolidone, or a mixture of the foregoing solvents, preferably DMF. The reaction temperature, which is highly dependent on the reagent used, can be from −78° C. to 60° C. In this step, $R^8$ is preferably a hydroxy protecting group such as an acetyl group, a benzyl group, or a trialkylsilyl group. To provide the compound of formula 6, deprotection of the C-2' hydroxy may proceed using methanol if $R^8$ is an acetyl group, hydrogenation if $R^8$ is an benzyl group, or fluoride anion, such as tetrabutylammonium fluoride, if $R^8$ is a trialkylsilyl group. The compound of formula 6 corresponds to the compound of formula 1 wherein $R^8$ is H.

Scheme 2 illustrates a method of preparing the compounds of the present invention by introducing the $R^{11}$ group at an early step in the synthesis of the final compounds. In step 1 of Scheme 2, a $R^{11}$ halo group may be introduced according to essentially the same procedure described above for Scheme 1. In step 2 of Scheme 2, the compound of formula 9 may be prepared by treating the compound of formula 8 with a base such as 1,8-diazabicyclo[5,4,0]undec-7-ene (DBU) and 1,1'-carbonyl-diimidazole (CDI) in methylene chloride. Treatment of the compound of formula 9 with hydrazine in acetonitrile at about 60° C. provides the cyclic carbazate of formula 10. Treatment of the compound formula 10 with O-alkylhydroxyamine in ethanol provides the oxime of formula 11. A reductive amination with an appropriate aldehyde of the formula $R^2$—C(O)H and deprotection, if desired, of the C-2' hydroxy group provides the compound of the formula 12 which corresponds to the compound of the formula 1 wherein $X^1$ is —NH— and $X^2$ is =$NOR^1$. The compound of formula 10 may also be converted to a compound of formula 14 wherein $X^1$ is —NH—, as indicated in step 4' of scheme 2 above, by treating the compound of formula 10 with an appropriate heterocycle, such as a substituted imidazole, and an α,β-unsaturated aldehyde such as acrolein in acetic acid followed by reduction with sodium borohydride.

Scheme 3 illustrates preparing compounds of the formula 13 which correspond to compounds of the formula 1 wherein $X^2$ is =O. In this process, the compound of formula 9 may be prepared as described above. The compound of formula 9 may be converted to the compound of formula 13 wherein $X^1$ is O, $CR^4R^5$, or $NR^4$ by treating the compound of formula 9 with $NH_2$—$X^1$—$R^2$ wherein $X^1$ is O, $CR^4R^5$, or $NR^4$.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula 1 that are acidic in nature are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |

-continued

| Strain Designation | Macrolide Resistance Mechanism(s) |
| --- | --- |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of formula 1 can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. mulftocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula 1, and the pharmaceutically acceptable salts and solvates thereof (hereinafter "the active compounds"), may be adminstered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The Examples provided below illustrate specific embodiments of the invention, but the invention is not limited in scope to the Examples specifically exemplified.

The Example provided below illustrates a specific embodiment of the invention, but the invention is not limited in scope to the Example specifically exemplified. In the following example, "Ac" represents an acetyl group, "Me" represents a methyl group, and "Et" represents an ethyl group.

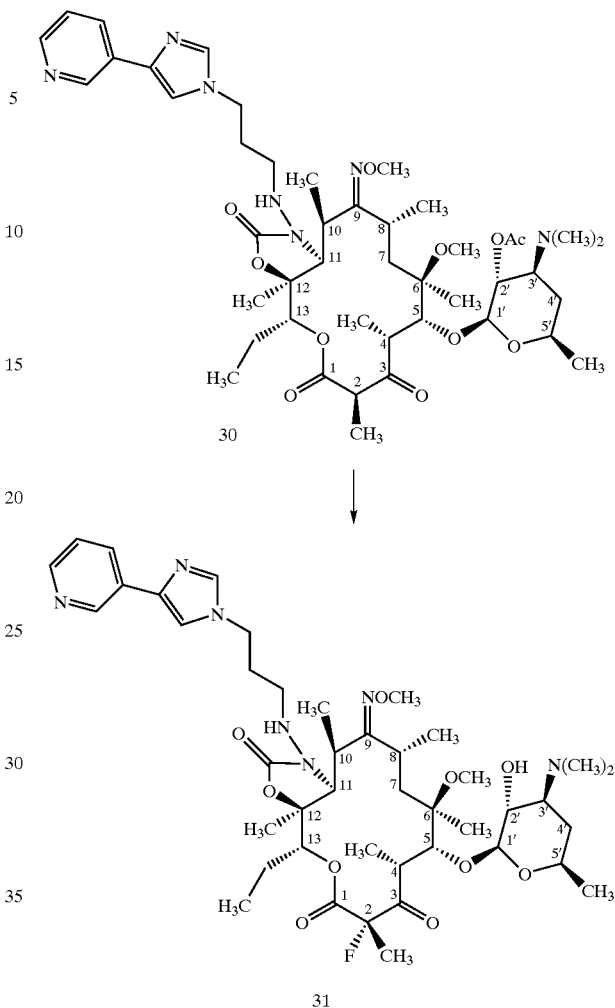

EXAMPLE 1

To a solution containing the compound of formula 30 above (wherein "Ac" represents an acetyl group)(513 mg, 0.58 mmol) in 5.8 mL of DMF were added at −78° C. 1.74 mL of 0.5 M solution of KHMDS in toluene (0.87 mmol). SELECTFLUOR™ (marketed by Air Products and Chemicals, Inc., Allentown, Pa., United States of America) (236 mg, 0.87 mmol) was added to this solution after 30 minutes of stirring at −78° C. Fresh SELECTFLUOR™ (27 mg, 0.076 mmol) was added after 30 minutes of stirring at −78° C. After an additional 30 minutes of stirring at the same temperature, the reaction mixture was diluted with EtOAc (ethyl acetate) and washed with water and brine. Drying over sodium sulfate and removal of the solvent gave 477 mg (93%) of a compound corresponding to formula 31 above except with the C-2' hydroxy protected with an acetyl group.

This material was dissolved in 50 mL of MeOH and warmed to 50° C. overnight. Evaporation of the solvent and chromatography on $SiO_2$ gave the compound of formula 31 (which corresponds to the compound of formula 2 referred to above wherein $R^{12}$, $R^{13}$, $R^{14}$ and $R^{15}$ are each H); NMR (CDCl3, δ) 8.93 (1H,d), 8.42 (1H, dd), 8.04 (1H, dd), 7.57 (1H,s), 7.35 (1H, d), 7.24 (1H, dd), 6.13 (1H, s), 4.89 (1H, dd), 4.28 (1H, d), 4.19 (2H,m), 4.07 (1H, d), 3.69 (3H, s), 3.66 (1H, s), 3.56 (1H, m), 3.48 (1H, m), 3.41 (1H, m), 3.24 (1H, m) 2.76 (1H, m), 2.60 (2H, m), 2.57 (3H, s), 2.36 (6H, s), 1.93 (2H, m), 1.74 (3H, d), 1.76–1.20 (6H, m), 1.49 (3H, s), 1.34 (3H, s), 1.27 (3H, d), 1.22 (3H, d), 1.11 (3H, d), 0.98 (3H, d), 0.83 (3H, t).

EXAMPLE 2

Following the procedures described in Scheme 2 above, a compound corresponding to formula 1 wherein $X^1$ is —CH(CH$_3$)(CH$_2$)$_2$—, $X^2$ is =NOCH$_3$, $R^8$ is H, $R^9$ is CH$_3$, $R^{10}$ is CH$_2$CH$_3$, $R^{11}$ is F, and $R^{12}$ is 4-(pyridin-3-yl)-imidazol-1-yl, was prepared. MS 874 (M+1)

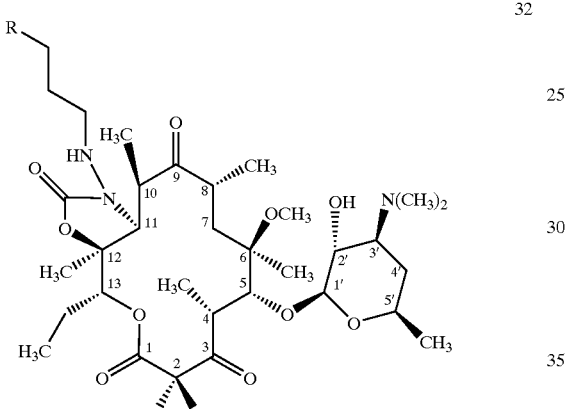

The following examples, which each had a structure according to formula 32 above, were prepared following the procedure below which describes the preparation of the compound of example 3. Examples 4 to 10 were prepared using the same procedure and using an appropriate heterocyclic compound in place of phenyl imidazole.

EXAMPLE 3

To a solution of compound 10 (100 mg, 0.155 mmole) and phenyl imidazole (67.0 mg, 0.465 mmole) in 1.5 mL of acetic acid was added 12.7 μL of 90% acrolein (0.171 mmol). The resulting mixture was stirred at room temperature overnight. Sodium cyanoborohydride (46.7 mg, 0.775 mmol) was then added and the solution was stirred at room temperature over night. The solution was diluted with water and its pH was adjusted to 10 with 40% aq NaOH solution. The aqueous solution was extracted with methylene chloride. The combine methylene chloride layer was dried over sodium sulfate and the solvent was removed under reduced pressure. The residue was purified by TLC (89% methylene chloride-10% methanol-1% ammonium hydroxide) to give 6 mg (5% yield) of example 3.

| Example | R | Mass Spec. (M + 1) |
|---|---|---|
| 3 | 2-phenylimidazol-1-yl | 830 |
| 4 | 4-(methoxycarbonyl)-5-(acetoxy)imidazol-1-yl (H$_3$COC(O)-, C(O)OCH$_3$) | 870 |
| 5 | 6-aminopurin-9-yl | 821 |
| 6 | 5-(4-chlorophenyl)tetrazol-2-yl | 867 |
| 7 | 4-(cyanomethyl)imidazol-1-yl | 793 |
| 8 | 5-phenyltetrazol-2-yl | 832 |
| 9 | 5-(2-chlorophenyl)tetrazol-2-yl | 867 |
| 10 | 4-(2-acetamidoethyl)imidazol-1-yl | 839 |

What is claimed is:
1. A compound of the formula:

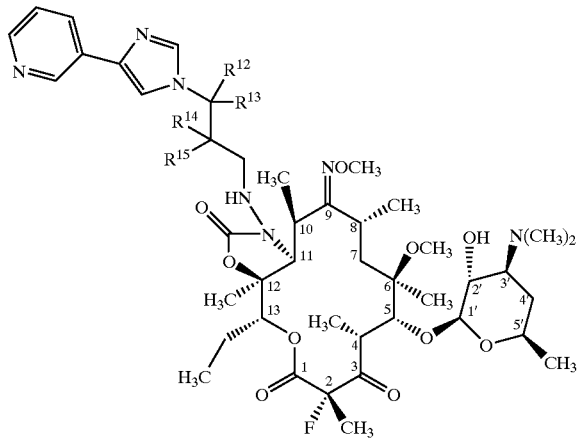

or a pharmaceutically acceptable salt or solvate thereof, wherein $R^{12}$, $R^{13}$, $R^{14}$ and $R^{15}$ are each independently selected from H, halo, methyl and ethyl.

2. A compound according to claim 1 wherein $R^{14}$ and $R^{15}$ are both H and $R^{12}$ and $R^{13}$ are each independently selected from H and methyl.

3. A compound according to claim 1 wherein $R^{12}$, $R^{13}$, $R^{14}$ and $R^{15}$ are each H.

4. A compound of the formula:

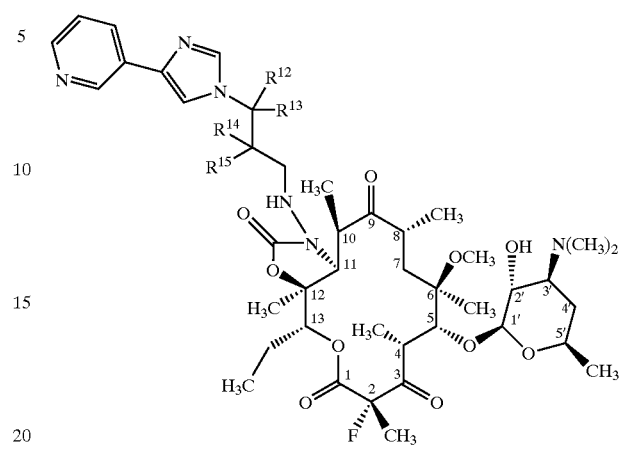

or a pharmaceutically acceptable salt or solvate thereof, wherein $R^{12}$, $R^{13}$, $R^{14}$ and $R^{15}$ are each independently selected from H, halo, methyl and ethyl with the proviso that at least one of $R^{12}$, $R^{13}$, $R^{14}$ and $R^{15}$ is not H.

5. A compound according to claim 4 wherein $R^{14}$ and $R^{15}$ are both H, $R^{12}$ is methyl, and $R^{13}$ is selected from H and methyl.

* * * * *